(12) United States Patent
Neubauer et al.

(10) Patent No.: US 7,776,048 B2
(45) Date of Patent: Aug. 17, 2010

(54) ADJUSTABLE TREATMENT AID FOR TREATING BONES

(75) Inventors: Timo Neubauer, Feldkirchen (DE); Norman Plassky, Erfurt (DE); Anusch Saffari, Schaftlach (DE)

(73) Assignee: BrainLAB AG, Feldkirchen (DE)

( * ) Notice: Subject to any disclaimer, the term of this patent is extended or adjusted under 35 U.S.C. 154(b) by 620 days.

(21) Appl. No.: 11/113,953

(22) Filed: Apr. 25, 2005

(65) Prior Publication Data

US 2005/0261699 A1    Nov. 24, 2005

Related U.S. Application Data

(60) Provisional application No. 60/564,795, filed on Apr. 23, 2004.

(51) Int. Cl.
  *A61B 17/58* (2006.01)
  *A61B 17/60* (2006.01)
  *A61F 2/00* (2006.01)

(52) U.S. Cl. .................. 606/96; 606/86 R; 606/87; 606/88

(58) Field of Classification Search .............. 606/96, 606/98, 88, 97, 130; 91/44; 83/745; 409/178, 409/179
See application file for complete search history.

(56) References Cited

U.S. PATENT DOCUMENTS 5,451,228 A * 9/1995 Johnson et al. ............... 606/86
5,681,316 A * 10/1997 DeOrio et al. ................ 606/88
5,833,693 A * 11/1998 Abrahami ..................... 606/96
6,030,211 A * 2/2000 Sandhaus ..................... 433/76
6,258,096 B1 * 7/2001 Seki ............................ 606/88
6,712,824 B2 * 3/2004 Millard et al. ............... 606/87
2001/0029377 A1 * 10/2001 Aebi et al. ................... 606/105
2004/0122436 A1 * 6/2004 Grimm ........................ 606/87
2005/0203528 A1 * 9/2005 Couture et al. ............... 606/86
2006/0155291 A1 * 7/2006 Farrar et al. .................. 606/87

FOREIGN PATENT DOCUMENTS

| DE | 202 19 357 | 2/2003 |
| DE | 102 07 035 | 9/2003 |
| EP | 1 249 213 | 10/2002 |
| WO | 2004/017843 | 3/2004 |

\* cited by examiner

*Primary Examiner*—Thomas C Barrett
*Assistant Examiner*—Andrew Yang
(74) *Attorney, Agent, or Firm*—Renner, Otto, Boisselle & Sklar, LLP (57) ABSTRACT

An adjustable treatment aid for guiding, holding, attaching and/or positioning a tool for treating a bone includes a first frame having a bone position fixing device to attach the first frame to the bone, and a second frame for guiding, holding, attaching and/or positioning the tool. At least one adjusting device allows the first frame to be spatially adjusted relative to the second frame along at least one degree of freedom.

15 Claims, 7 Drawing Sheets

ADJUSTABLE TREATMENT AID FOR TREATING BONES

RELATED APPLICATION DATA

This application claims priority of U.S. Provisional Application No. 60/564,795 filed on Apr. 23, 2004, which is incorporated herein by reference in its entirety.

FIELD OF THE INVENTION

The present invention relates to guiding and/or positioning a tool for treating a bone and, more particularly, to guiding an incision tool or drill for osteoresection and/or for guiding and/or positioning a medical operating instrument.

BACKGROUND OF THE INVENTION

When attaching implants, such as, for example, artificial knee, elbow, finger or hip joints, it is necessary to position the implant as exactly as possible on the adjacent bone. To this end, incisions and/or bores are made, typically on the bone structures adjacent to the implant.

For example, a precise incision on the bone is necessary in knee arthroplasty to achieve maximum stability and resilience of the implant. To this end, a tool, such as an incision block, serves as a template for the cutting process and must be precisely placed on the bone in order to achieve an exact resection. Once placed on the bone, the incisions are made and the implant can be attached to the bone.

Computer-assisted surgery (CAS) is a tool often used by surgeons to assist during surgical procedures. When using CAS, the bone structure of the patient is known to a navigation system following a reading-in procedure. CAS, via a display, provides visual feedback to the surgeon of the location of the bone with respect to tools and/or instruments, such as incision blocks and/or other devices (e.g., stability rods, tools, clamps and the like, any of which may be external to the bone structure or run intramedullarily in the bone). The surgeon uses the visual feedback to place or otherwise position the incision block on the bone such that cutting planes formed by the incision block are in a desired location. Moreover, CAS allows the surgeon to view the location of the other devices on or in the bone structure with respect to the cutting planes of the incision block. In doing so, the surgeon can avoid placing the incision block such that the cutting planes intersect or otherwise encroach the devices on or in the bone.

For example, during surgery the surgeon places the incision block on the bone by freehand and, once in the desired location, the surgeon fixes the incision block to the bone. More particularly, the surgeon places the incision block on the bone and, using the visual feedback provided by the CAS, alters the angle, position, etc. of the incision block with respect to the bone such that one or more cutting planes of the incision block are in a desired location. Once the cutting planes are in the desired location, the incision block is rigidly fastened to the bone using fastening means, such as screws, nails or the like.

Unfortunately, it often is difficult to maintain the precise position of the incision block as it is fastened to the bone. Often, the final precision of the incision block placement depends on the ability of the surgeon, despite the assistance of CAS.

Accordingly, it would be advantageous to provide an apparatus wherein the final position of the tool is independent of the surgeon's abilities.

SUMMARY OF THE INVENTION

According to one aspect of the invention, an adjustable treatment aid for guiding, holding, attaching and/or positioning a tool for treating a bone, comprises a first frame that includes a bone position fixing device to attach the first frame to the bone; a second frame for guiding, holding, attaching and/or positioning the tool; and at least one adjusting device that allows the first frame to be spatially adjusted relative to the second frame along at least one degree of freedom.

Another aspect of the invention, an adjustable treatment aid for guiding, holding, attaching and/or positioning a tool for treating a bone comprises a sub-frame; a first elongated member coupled to the sub-frame; an interface for guiding, holding, attaching and/or positioning the tool; a first joint coupling the first elongated member to a first portion of the interface; a first setting wheel operatively coupled to the first elongated member; and a second joint coupling the first setting wheel to a second portion of the interface, wherein as the first setting wheel is rotated about the first elongated member, a spatial relationship between the interface and the sub-first frame is adjusted along at least a first and second degree of freedom.

The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The foregoing and further features of the present invention will be apparent with reference to the following description and drawings, wherein:

FIG. 5b is a back isometric view of a treatment aid of FIG. 5a;

DETAILED DESCRIPTION

The present invention relates to an adjustable treatment aid for treating a bone. The treatment aid serves to guide, hold, attach and/or position a tool that can be used for treating a bone. The tool can include templates and/or guides that guide a bone treatment tool, such as, for example, an incision tool or a bone drill. The tool, however, also can be the bone treatment tool itself, e.g., a drill or the incision tool. The drill can be a mechanical drill or another type of drill, such as, for example, a laser drill or a water jet drill. Similarly, the incision tool need not operate mechanically. For example, the incision tools can cut by means of a laser beam or a water jet.

Figure 1:
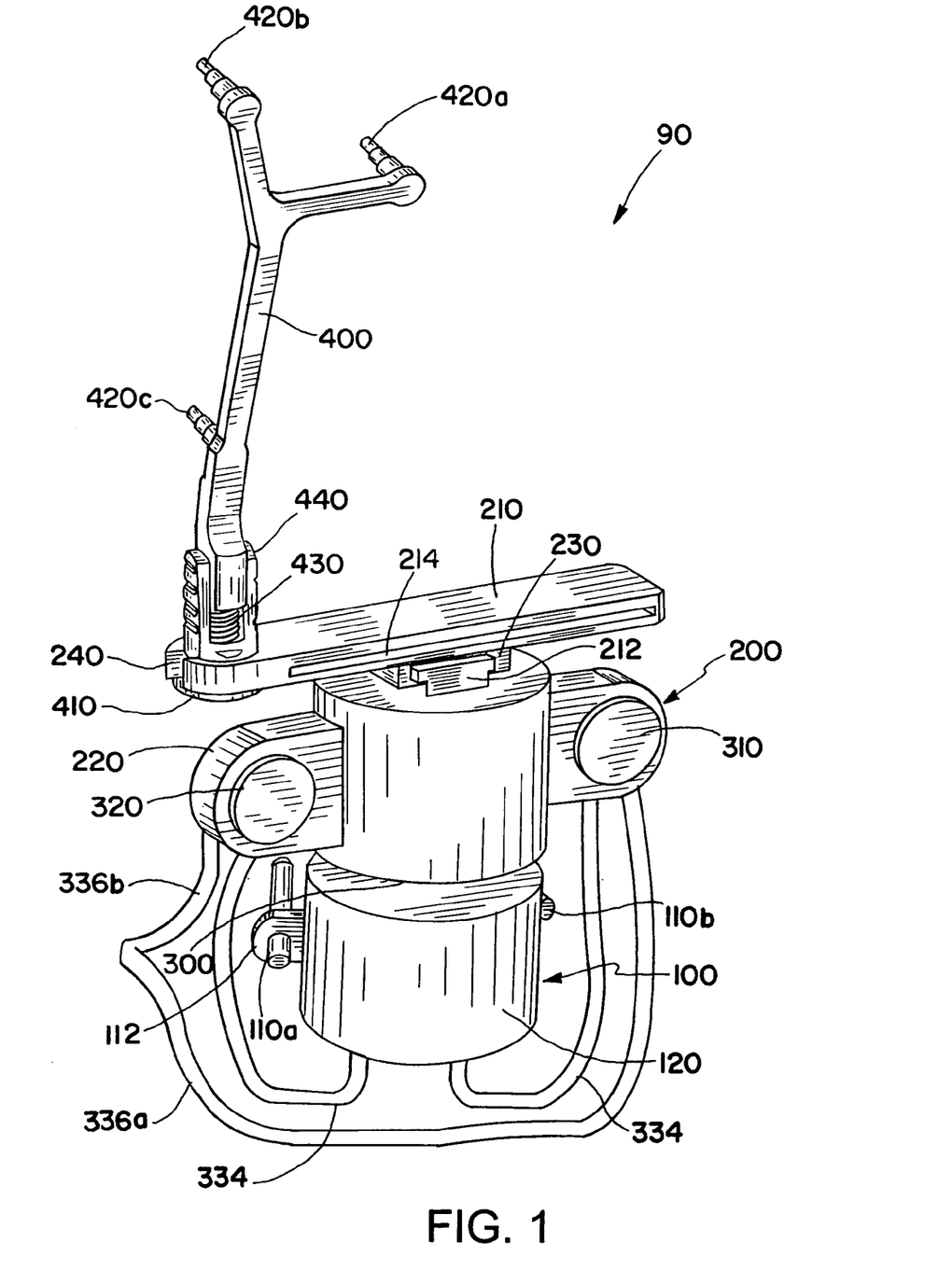
FIG. 1 is an isometric view of a treatment aid in accordance with an embodiment of the invention.

With reference to FIG. 1, an exemplary treatment aid 90 in accordance with the invention includes a first frame 100 that can be fixed to a bone. The first frame 100 can include a bone position fixing device, such as, for example, loops 112 through which fixing means, such as positioning pins 110a, can be guided into the bone. Similarly, the bone position fixing device can include a threaded bore (not shown), such that a screw can be inserted through the bone and into the bore to fix the first frame 100 to the bone. Also, the bone position fixing device itself can be fitted with means which can be inserted directly into the bone to fix the first frame to the bone, such as the aforesaid positioning pins or screws, for example. If two or more fixing means (e.g., positioning pins and/or screws) are provided, then the fixing means can be aligned parallel with their respective longitudinal direction. The fixing means can run obliquely with respect to each other to improve a holding force to the bone.

The treatment aid 90 further includes a second frame 200, which serves to guide, hold, attach and/or position a tool, and an adjusting device 300 for spatially adjusting and/or setting the relative position of the first frame 100 with respect to the second frame 200.

The first frame 100 can move relative to the second frame 200 along three different degrees of freedom. The first frame can rotate about two axes that are oblique or orthogonal with respect to each other. Each of the degrees of freedom can be used for adjusting the position between the first and second frame and, therefore, are referred to herein as "adjustment degrees of freedom". The adjustment degrees of freedom can correspond to a translational movement of the first frame relative to the second frame and can serve to determine an inclination, varus/valgus and the resection level during bone treatment.

As will be described in more detail below, a relative movement between the first and second frame (along at least one of the adjustment degrees of freedom) can be blocked or locked when a force acts on the first frame 100 or the second frame 200. The force required to overcome the lock preferably is larger than forces that are applied to the adjusting device during the treatment procedures. This ensures that the tool is securely placed, even when vibration forces due to a sawing or a drilling process, for example, act on the treatment aid 90.

The adjusting device 300, which is coupled to the treatment aid 90, provides an adjusting force such that relative movement between the first frame 100 and the second frame 200 can be achieved. The adjusting device 300 can be self-locking, such that an adjusting movement is enabled when the adjusting device 300 is unlocked, and an undesired adjusting movement is disabled or counteracted when the adjusting device is locked. A separate adjusting device can be provided for each degree of freedom. The adjusting force produced by the adjusting device 300 should be smaller than a locking force of the adjusting device. For example, the locking force can be more than 2, 5, 10, 20, 50 or 100 times greater than the adjusting force necessary for adjusting the relative positions of the first and second frame.

Once an adjusting process is complete, the adjusting device 300 is fixed or semi-fixed via a positive lock and/or by means of a force that causes a deformation. As a result, a lock is achieved that prevents or tends to inhibit relative motion between the first and second frames. Elastic means can be provided that can be easily deformed by the adjusting device, but whose elastic force acts such that a disturbance of the adjusting device 300 due to a transfer of force (via the first and/or second frame) is counteracted.

The adjusting device 300 can alternate between an adjustable and a non-adjustable state. This can be achieved, for example, using a non-positive lock having an elastic means and/or via a positive lock. The adjusting device 300 can be controlled pneumatically, hydraulicly or electrically.

As will be described below, the adjusting device 300 can include rotary joints, e.g., ball joints, that enable movement along at least one of the degrees of freedom. A single rotary joint enables two degrees of freedom of rotation.

In addition or as an alternative to joints, the adjusting device 300 can include an elastic or bending structure that is designed such that bending of the structure corresponds to the movement of a joint. In particular, the adjusting device 300 can include an elastic structure having predetermined bending points that are tapered or formed from a softer or more flexible material. The points can be chosen such that forces of the adjusting device has an amplified effect, e.g. via a lever effect. The elastic structure can be formed as one piece to facilitate cleaning and to lower cost, and can be made of elastic materials, such as plastic, for example.

A treatment block 210 can be fixed to the second frame 200 such that the treatment block can be moved, positionally fixed or detached from the second frame. The treatment block 210 can be integrally formed with the second frame 200, or it can be a discrete assembly that is releaseably coupled to the second frame. The treatment block can serve to guide an incision movement of an incision tool or a drilling movement of a drilling tool. As an alternative (or in addition) to the above treatment block 210, a tool (not shown), such as, for example, an incision tool or a drilling tool, can be fixed to the second frame 200, such that the tool can be moved, positionally fixed or detached from the second frame. As was described above with respect to the treatment block 210, the tool can be integrally formed with the second frame 200, or it can be a discrete assembly that is releaseably coupled to the second frame.

A navigating device 400 can be provided to the second frame 200 that allows the position of the second frame to be identified. The navigating device can operate together with a navigation system (not shown) to which the position and surface characteristics of the bone to be treated can be ascertained. The navigating device 400 can be a reference star, for example, wherein the reference star includes passive markers 420a, 420b, 420c that can be detected by the navigation system. The passive markers reflect electromagnetic waves, e.g., light, infrared rays, UV light, etc. or ultrasound, for example. The navigating device 400 can be geometrically formed such that the position of the navigating device can be detected by identifying the location of the markers 420a, 420b, 420c. The navigating device 400 can be releaseably coupled to the treatment aid 90, the treatment block 210, or the tool, such that it can be positionally fixed with respect to the second frame 200. The navigating device 400 also can be formed as one piece with the treatment aid 90, the treatment block 210 or the tool.

The navigating device 400 can include a mechanical contact interface 410 for contacting a surface, e.g., a surface of the tool and/or the treatment block 210. As will be described below, the mechanical contact interface 410 facilitates identifying the position of the bone and, in particular, the incision area of the bone or a surface of the bone.

With continued reference to FIG. 1, the treatment aid can use pneumatic force (alternatively, for example, hydraulic force) to release a catch or block of the adjusting device 300. The exemplary treatment aid 90 includes a first casing 120 that forms part of the first frame 100, while a second casing 220 forms part of the second frame 200. The first casing 120 and the second casing 220 are connected via the adjusting device 300. As will become evident below, a part of the adjusting device 300 is situated within the first casing 120, while another part of the adjusting device 300 is situated within the second casing 220.

Flexible tubes 332, 334 carry fluid or gas, e.g., hydraulic fluid or air, into the first and second casings 120, 220 to the adjusting device 300. First and second valves 310, 320 control fluid flow through flexible tubes 332, 334, thereby pneumatically (or hydraulically) controlling the adjusting device 300, as is explained in more detail below in connection with FIG. 2. A rail 230 forms a mechanical interface to the treatment block 210. The treatment block 210 and the interface 230 can be formed such that a fixed position, such as the distance to the bone to be treated, can be set. A notch, for example, can be provided along a carriage 212 of the treatment block 210, such that the carriage can slide along the rail 230, and the notch meshes with a locking element (not shown) outside the rail 230. This permits the treatment block 210 to slide forward towards the bone until a desired position has been reached, e.g., a very close position or a contact position between the treatment block and the bone. The notch can be formed such that the treatment block 210 cannot be retracted until the entire treatment aid 90 has been detached from the bone. For example, the notch can be formed such that the bone prevents the treatment block 210 from advancing in a forward direction, and the notch prevents the treatment block from advancing in a reverse direction, thereby preventing the treatment block from being removed from the treatment aid 90.

The first casing 120 of the first frame 100 can be connected to the bone via pins 110a and 110b, which can be guided through loops 112. The pins 110a, 110b and loops 112 can be configured such that the pins are pressed into the loops, thereby creating an interference fit, or, alternatively, a non-interference fit between the pins and loops can be incorporated. The loops 112 can be connected and positionally fixed to the casing 120. Alternatively, a screw, for example, can be provided that interfaces with a bore having an inner thread that corresponds with the threads of the screw. Other methods of fastening are contemplated, including, for example, adhesion or hooks.

The treatment block 210 can be an incision block having a slit 214 through which an incision tool, such as a saw blade, for example, can be guided. A navigating device 400, such as a reference star 400, is releaseably coupled to the treatment block 210. At its base, the reference star 400 includes a contact plate 410 which, when the reference star 400 is detached from the treatment aid 90, can be brought into contact with an incision area of the bone. More particularly, the contact plate 410 can be placed flat on the incision area of the bone to measure or otherwise determine the position of the incision area. The reference star can include three passive markers 420a, 420b, 420c that span a plane. The connection between the reference star 400 and the treatment block 210 can be formed by a latch connection that includes an elastic means 430, such as a spring, for example. The elastic means 430 can be guided about an axis of the reference star 400. The elastic means 430 presses a sleeve 440 of the reference star 400 down into a cavity on the treatment block 210, resulting in a positive lock between the reference star and the treatment block. As the sleeve 440 is raised against the spring force 430, the positive lock is released and the axis surrounded by the spring 430 can be guided out laterally through the slit 240 in the treatment block 210.

Figure 2:
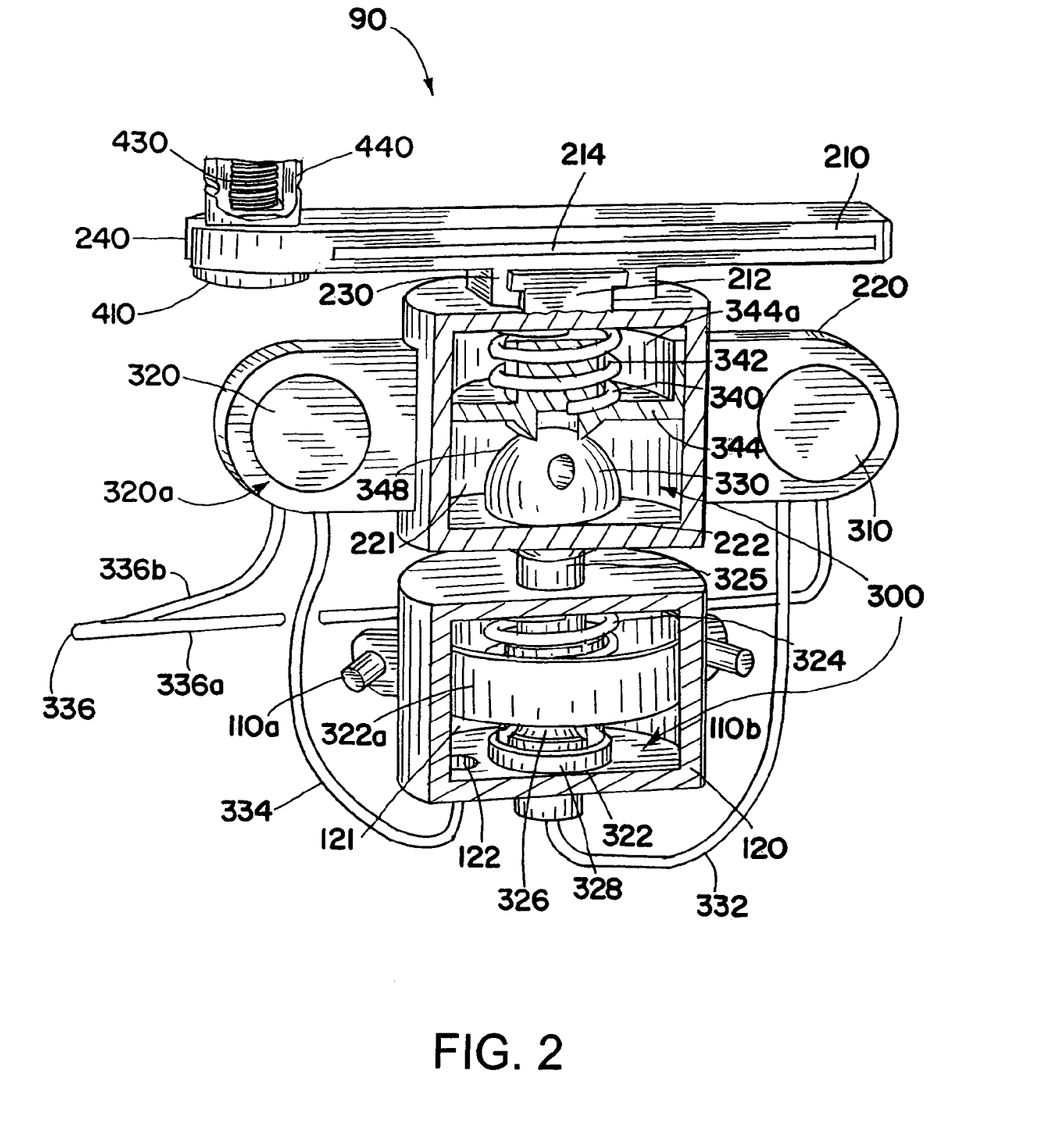
FIG. 2 is a sectional view of the treatment aid of FIG. 1.

With further reference to FIG. 2, a cutaway of the treatment aid 90 is shown, illustrating the features of the adjusting device 300. Pressurized air is supplied to the adjusting device 300 via the flexible tube 336, which is split into two flexible tubes 336a, 336b. The flexible tube 336b guides the pressurized air to the second valve 320, which can be opened or activated by pressing on a first button 320a.

If the second valve 320 is opened, then the pressurized air, via the flexible tube 334, continues into the interior of the first casing 120 through a first opening 122. The pressurized air in the interior of the first casing 120 causes a sealing disc 322 to rise, which can slide air-tight along an inner wall of the first casing 120, thereby preventing air from passing upwards. The sealing disc 322, which is pressed down by a first elastic element, such as a first spring 324, acts via a pressing ring 326 on a deformable conical disc 328. The first spring 324 axially surrounds an axis 325, which, at least in the region of the conical disc 328, includes grooves or notch recesses that run radially about the axis 325. The grooves or notch recesses mesh with the conical disc as the conical disk is deformed by pressure exerted by the first spring 324 and pressing ring 326. The sealing disc 322, the pressing ring 326 and the conical disc axially surround the axis 325 and can be moved along the axis.

If pressurized air is introduced into the chamber of the first casing 120 through the first opening 122, then the sealing disc 322 raises and the pressing ring 326 no longer presses on the conical disc 328. Since the pressing force is removed from the conical disc 328, the conical disk is no longer deformed and does not mesh with the notch recesses or grooves of the axis 325. The axis 325 thus can be freely moved relative to the first casing 120 by a surgeon, for example. Therefore, a translational movement of the second casing 220 relative to the first casing 120 can be enabled by supplying pressurized air via the second valve 320.

A globe or sphere 330, which is fixedly connected to the axis 325, interfaces with a fraised-in sphere 222 of the second casing 220. The spherical opening 222 can exhibit a smaller diameter than the globe 330 and can be below the meridian of the globe 330. The second casing 220 can be connected to the globe 330 via a non-positive lock and/or a positive lock. This can be achieved, for example, by means of a second elastic element, such as a second spring 340, which can be axially mounted about the axis 342. The axis 342 is connected to a sliding element 344 as one piece within the second casing 220, wherein the sliding element 344 seals a lower chamber within the second casing at the top and includes a stopper 344a, such that a meshing tip 346 of the sliding element can only be removed from the globe 330 by a predetermined distance.

Similar to the sealing disc 322, the sliding element 344 slides air-tight along an inner wall of the second casing 220, thereby forming a seal. The first casing 120 and the second casing 220 can be formed to be cylindrical in shape. The meshing tip 346, which is tapered as it nears the globe 330, can be provided at a lower end of the sliding element 344 and includes a cylindrical recess 348 at its lower end. The tips of the sliding element 344 are pressed against a surface of the globe 330 by the spring force created by the second spring 340. In addition to a non-positive lock, the surface of the globe 330 can be deformed to achieve a positive lock.

If pressurized air is supplied to the first valve 310 via the flexible tube 336 and the first valve 310 is open, then air enters the axis 325, which is formed hollow, via the flexible tube 332. The pressurized air, which can be guided through a cylindrical hollow space of the interior of the axis 325, enters the inner space of the second casing 220 through an opening 331 (FIG. 4) in the globe 330. More specifically, the pressurized air enters a lower inner space or chamber 221 above which the element 344 lies. The pressurized air then exerts a force on the sliding element 344 that counteracts the force of the second spring 340. In this way, the tip 346 is disengaged from the globe and the second casing 220 is no longer pinched between the tip 346 and the spherical opening 222, such that the casing can be freely rotated about the globe 330 (two degrees of freedom of rotation).

The first and second chambers 121, 221, which are sealed at the top by the sealing disk 322 and sliding element 344, respectively, can be filled with pressurized air. The pressure contained within the chambers 121, 221 can be reduced via the flexible tubes that supply the pressurized air, or by openings provided in each of the first and second casings 120, 220. The openings allow the pressurized air to slowly escape, such that the pressure is automatically reduced when the first and second valves 310, 320 are closed. This reduction in pressure results in the adjusting device 300 being arrested. More specifically, as the pressure bleeds out of the chambers 121, 221, the tip 346 again presses on the globe 330, thereby inhibiting a first adjustment degree of freedom, and the conical disc 328 again is compressed, such that it meshes with the grooves of the axis 325, thereby inhibiting a second adjustment degree of freedom.

Figure 3:
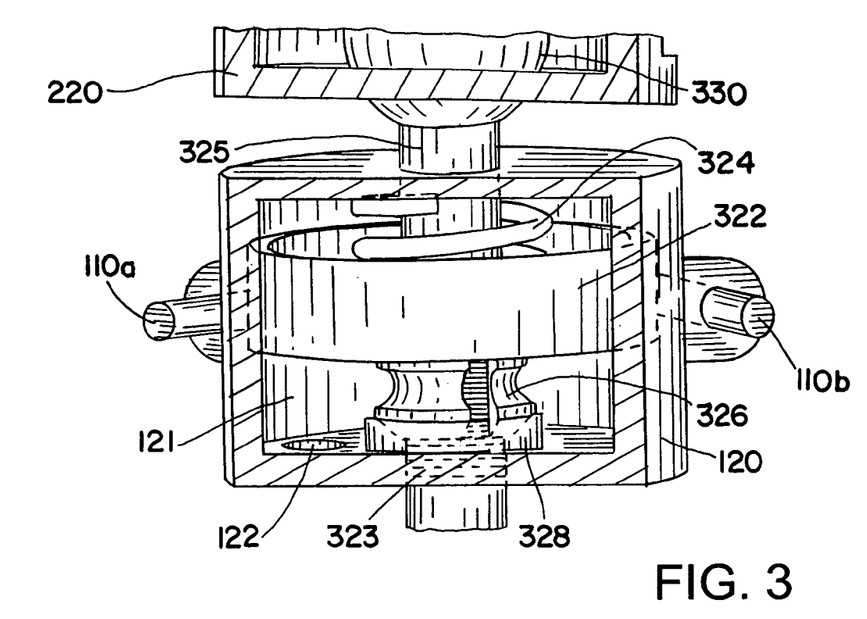
FIG. 3 is a detailed view of the adjusting device of FIG. 1.

FIG. 3 specifically shows the portion of the adjusting device 300 responsible for translational movement. The pressing ring 326 is shown exposed, such that the groove structure 323, which runs along the axis 325, can be seen. If the pressing ring 326, which is likewise formed conically at its lower end, presses on the conical disc 328, which is formed annularly at its lower end, then the conical disk 328 is compressed since it is formed elastically. More specifically, the lower annular end of the conical disk 328 is pressed between the grooves 323, thus preventing a translational movement of the axis 325 relative to the first casing 120.

The influx of pressurized air through the first opening 122 and into the first chamber 121 raises the sealing disc 322, such that the conical disc 328 is no longer pressed and, thus, no longer deformed. More specifically, the pressing ring 326, which is connected to the sealing disc 322, is raised upwards by the pressurized air acting on the sealing disc 322. Since the conical ring 328 no longer meshes with the grooves 323, the axis 325 can be freely shifted relative to the first casing 120.

Figure 4:
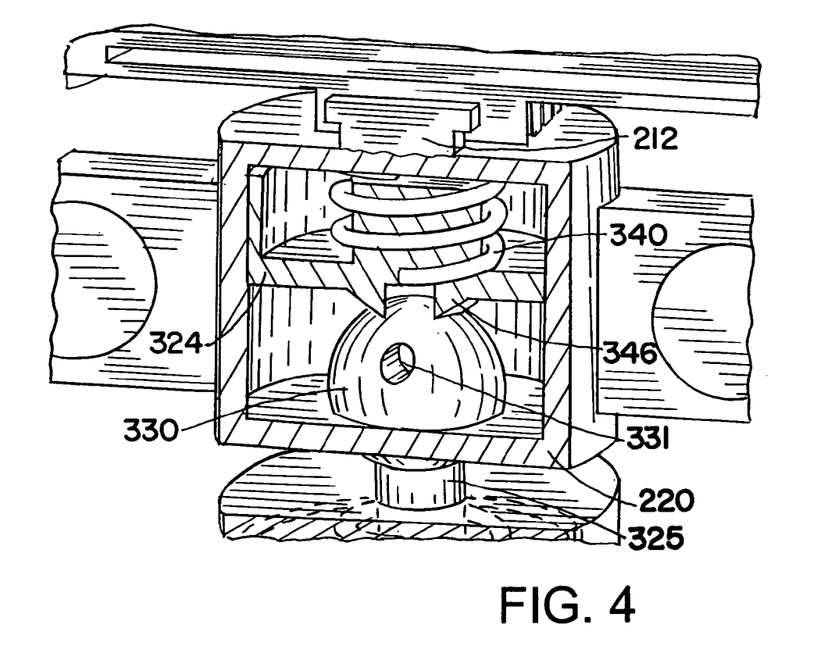
FIG. 4 is a sectional view of the embodiment illustrated in FIG. 3.

FIG. 4 is an enlarged view of the rotational part of the adjusting device 300. The opening 331 in the globe 330 through which the pressurized air escapes can be clearly seen.

Figure 5A:
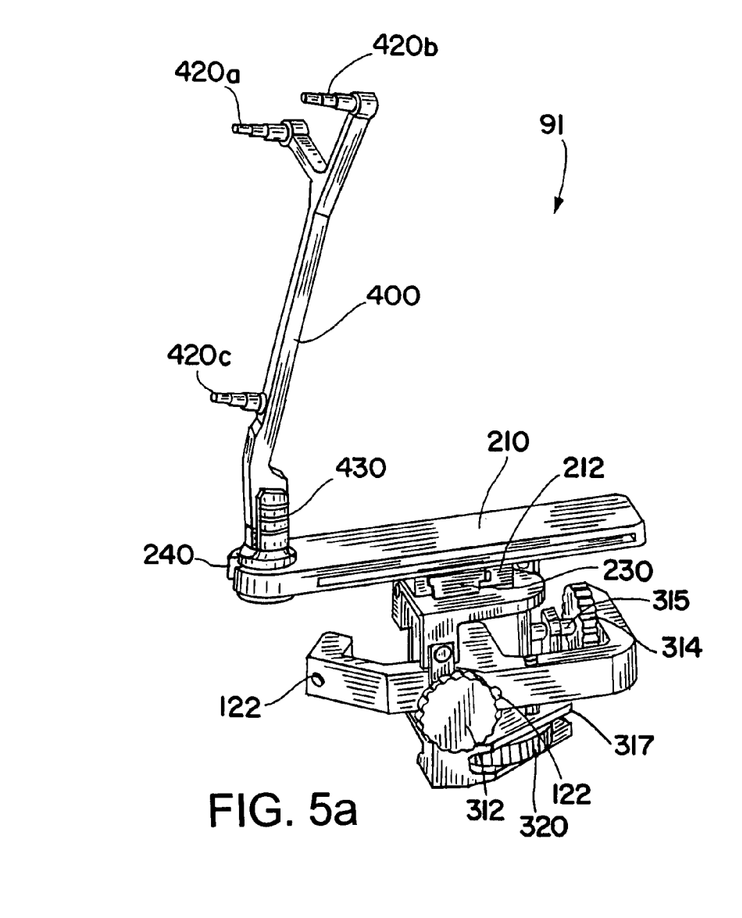
FIG. 5a is a front isometric view of a treatment aid in accordance with another embodiment of the invention.
Figure 5B:
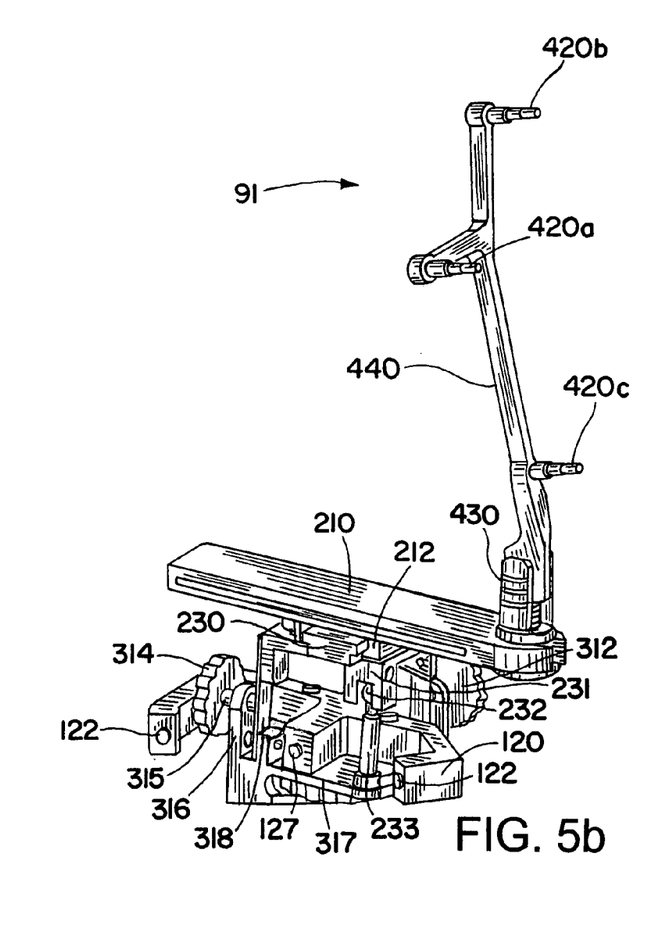

FIGS. 5a and 5b illustrate a second embodiment of the treatment aid 91 in accordance with the invention. FIG. 5a illustrates a view of the treatment aid 91 from the surgeon's point of view, e.g, a front view, while FIG. 5b illustrates a view of the treatment device a surgeon would not see, e.g., a back view.

As opposed to the first embodiment, the second embodiment 91 operates mechanically, instead of pneumatically. More specifically, elastically formed elements serve to fix the relative position between the first and second frames and, in particular, to secure the first and second frames as an external force is applied to the frames.

A first frame 120 includes openings 122 through which positioning pins can be guided to connect the first frame to the bone. First and second setting wheels 312, 314 can be used to provide a rotational force to first and second threaded rods, respectively (the second threaded rod 315 corresponds to the second setting wheel 314, while the first threaded rod, which corresponds to the first setting wheel 312, is not shown). The second threaded rod 315 runs in a complementary thread of a threaded rod mounting 316, which is connected and positionally fixed to a lower frame structure 317. One end of a deformable element 318, such as a leaf spring, for example, is attached to the lower frame structure 317 and the other end of the deformable element 318 is attached and positionally fixed to a rail 230. The rail 230 serves as an interface to the treatment block 210 via an upper frame structure 231. The upper frame structure 231 is connected to a ball joint 232, such that the upper frame structure can rotate about the ball joint 232. The ball joint 232 is situated at a distance from the lower frame structure 317, wherein the distance is fixed by a rod 233.

As the threaded rod 315 is rotated via the second setting wheel 314, it travels in or out of the threaded rod mounting 316. One end of the threaded rod 315 contacts the deformable element 318, thereby bending the deformable element as the rod moves in or out of the threaded rod mounting 316. Since the deformable element 318 is coupled to both the lower frame structure 317 and the upper frame structure 231, bending the deformable element 318 results. More specifically, as the deformable element bends, the distance between the lower frame structure 317 and the upper frame structure 231 in the region of the deformable element 318 is shortened. As the distance is shortened, the upper frame structure 231 rotates about the ball joint 232, which in turn inclines the interface and/or the rail 230, and therefore the treatment block 210, about the ball joint 232.

The first setting wheel 312, which is arranged analogously to the second setting wheel, acts on another deformable element 319 (FIG. 6) in the same manner as the second setting wheel 314 operates on the deformable element 318. The threaded rod assigned to the first wheel 312 can point toward the ball joint 232 or toward a mounting 233 for the ball joint 232. The axes of both threaded rods can be at right angles or oblique with respect to each other. In such a configuration, an acting force of the threaded rod assigned to the first setting wheel 312 causes the treatment block 210 to be inclined about the ball joint 232, independent and at a right angle to the inclination that can be caused by the second setting wheel 314, thus achieving two rotational degrees of freedom of adjustment.

While the first and second setting wheels 312, 314 cause a rotational movement about two axes perpendicular to each other, a third setting wheel 320 allows a translational movement. To this end, a thread (not shown) is formed in the first frame 120, and a third threaded rod (not shown), which is assigned or otherwise connected to the third setting wheel 320, meshes or interfaces with the thread of the first frame 120. The third setting wheel 320 also is connected to the lower frame structure 317, such that when a distance between the third setting wheel 320 and the first frame 120 is changed, a corresponding change in distance between the lower frame structure 317 and the first frame 120 also is achieved.

For example, the lower frame structure 317 can be formed such that it is slaved by the third setting wheel 320. As the third setting wheel 320 moves in relation to the first frame 120, the lower frame structure 317 also moves in relation to the first frame 120. Thus, rotating the third setting wheel 320 causes the third threaded rod to rotate, thereby altering a distance between the third setting wheel 320 and the first frame 120. As the distance between the third setting wheel 320 and the first frame 120 is altered, the distance between the first frame 120 and the lower frame structure 317 also is altered.

In another embodiment, the third setting wheel 320 includes an inner thread, wherein the third wheel 320 can be rotated about the third threaded rod. The third threaded rod is attached and secured against rotation to the first frame 120 or is formed as one piece with the first frame 120. As the third wheel 320 is rotated, it travels along the third threaded rod. Thus, a distance between the third setting wheel 320 and the first frame 120 can be altered by rotating the third setting wheel 320. Since the lower frame structure 317 is slaved by the third setting wheel 320, a distance between the first frame 120 and the lower frame structure 317 also can be altered. As will be appreciated, the alternative embodiment described with respect to the third setting wheel can be applied to the first and second setting wheels.

Figure 6:
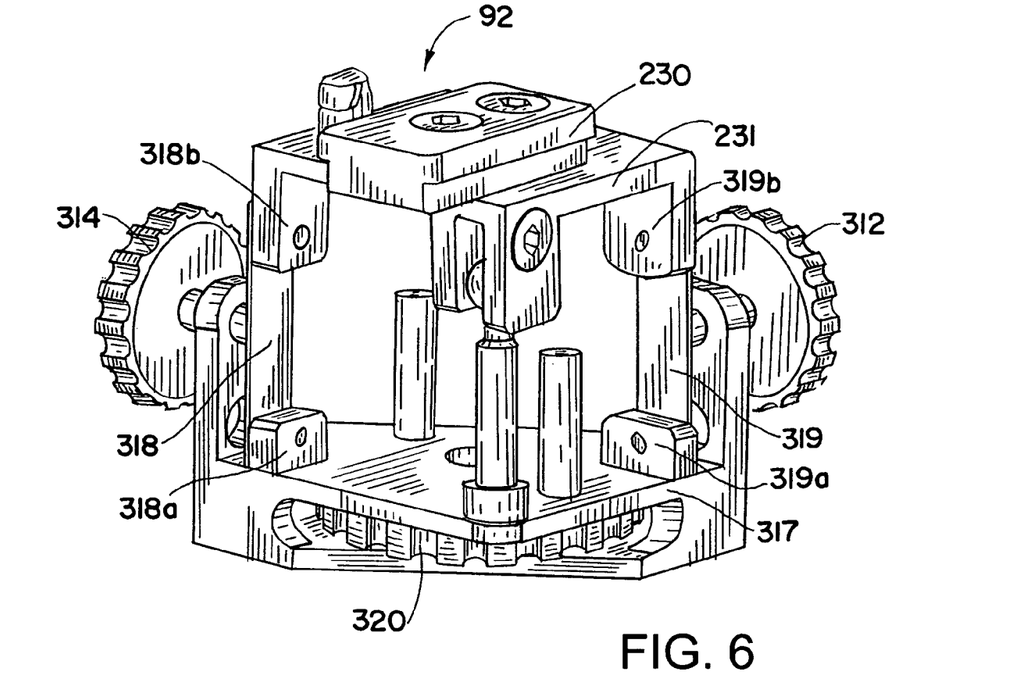
FIG. 6 is a detailed isometric view of the embodiment of FIGS. 5a and 5b.

FIG. 6 illustrates a variant of the treatment aid 92, wherein the deformable elements 318, 319 are connected to the upper frame structure 231 and the lower frame structure 317 via joints 318a, 318b, 319a, 319b, respectively. This enables an inclination along the rotational axes. The joints can be pins that are fastened to the upper and lower frame structures, e.g., screwed or pressed into the respective frame structures. The fit with respect to the deformable elements 318, 319 should allow some degree of movement so as not to bind or otherwise prevent movement of the joints 318a, 318b, 319a, 319b.

Figure 7:
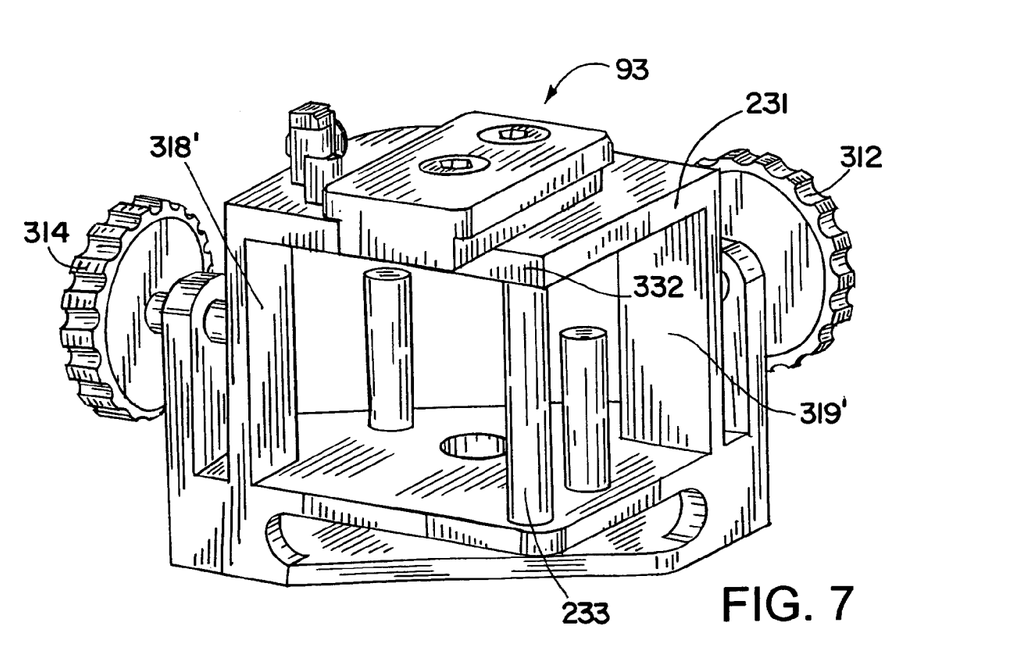
FIG. 7 is a detailed isometric view of the treatment aid in accordance with another embodiment of the invention.

FIG. 7 illustrates another variant of the treatment aid 93, wherein the deformable elements 318', 319' are integrally formed with the upper and lower frame structures. More particularly, the entire structure, except for the setting wheels, is formed as one piece with the assigned threaded rods. The portion of the structure that is deformed by the setting wheels can be formed with thin walls and/or a plastic material. The action of the force of the threaded rods on the thin walls of the deformable elements 318', 319' bends the deformable elements 318', 319', resulting in a rotational movement about a connecting point 332 between the upper frame structure 231 and a rod 233. The rod 233 also can be formed thin in order to enable the rod to be bent. In this way, a rotational movement about two axes perpendicular to each other can be achieved. Moreover, the number of components of the treatment aid 93 can be reduced, which is advantageous for cleaning the treatment aid.

Figure 8:
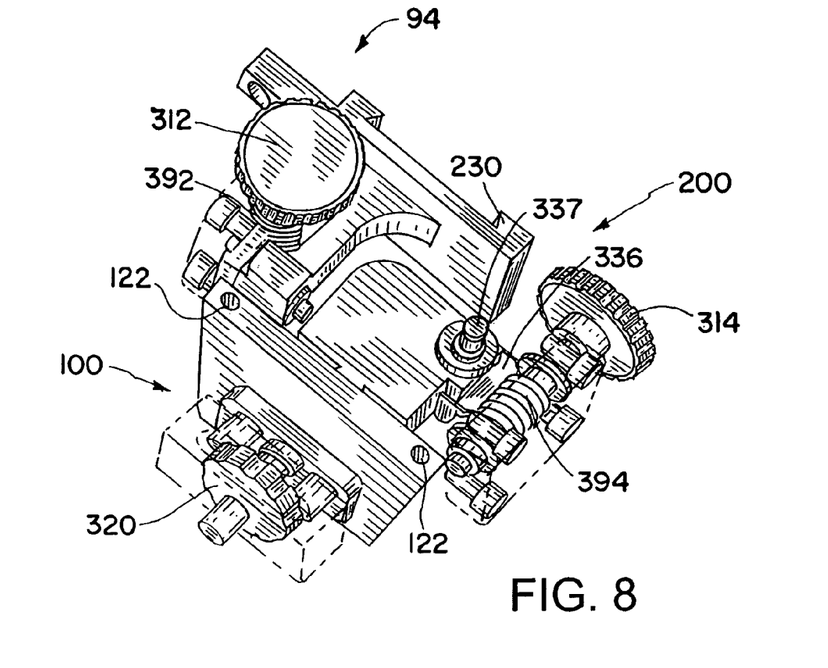
FIG. 8 is an isometric view of the treatment aid in accordance with another embodiment of the invention.

FIG. 8 illustrates a third embodiment of the treatment aid 94, which uses a self-locking gear, such as a worm gear, for example, to adjust the rotational axes. A first worm gear 392 is activated by the first setting wheel 312 and a second worm gear 394 is activated by the second setting wheel 314. The worm gears 392, 394 are mounted to a bearing (not shown), which is connected and positionally fixed to the second frame 200. The first and second worm gears 392, 394 each mate with a first and second gear wheel, wherein only the second gear wheel 336 is shown. The axes of the gear wheels are arranged at a 90 degree angle to the axes of the worm gears. The gear wheels cause a rotation about a first rotational axis 337 and about a second rotational axis (not shown), each of which runs perpendicular to the axis of the respectively assigned worm gear. This again achieves the desired two rotational degrees of freedom of adjustment.

Figure 9:
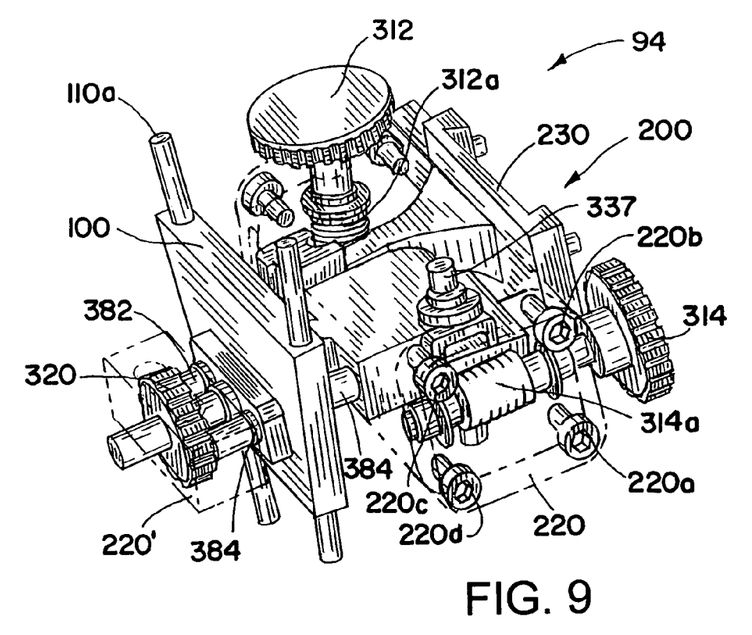
FIG. 9 is another isometric view of the embodiment of FIG. 8 taken from a different vantage point.

With further reference to FIG. 9, the adjusting device responsible for rotation, such as the worm gears, the assigned gear wheels and the rotational axes, are arranged within a casing 220 that is fixedly attached to a frame structure (not shown) using fastening means, such as screws 220a-220d. The frame structure can be connected as one piece to the interface to the treatment block. This is advantageous, for example, in that it facilitates cleaning of the treatment aid 94.

A translational movement is achieved with the aid of the third setting wheel 320. As in the embodiment of FIG. 7, the treatment aid 94 can be formed as one piece, wherein a threaded rod runs in a complementary thread of the structure, and rotates with the third setting wheel 320. The complementary thread can be formed in the first frame 100. Openings 122 again are situated in the first frame 100, through which the positioning pins 110a and 110b can be guided (see FIG. 9). Another casing 220' surrounds the third setting wheel 320, wherein the third setting wheel protrudes through an opening of the casing 220'. The distance between the third setting wheel 320 and the first frame 100 can be set by rotating the third setting wheel 320. The third setting wheel 320 is connected and positionally fixed to the interface 230 via two rods 382, 384, and to the treatment block via the frame structure (not shown). Altering the distance between the third setting wheel 320 and the first frame 100 also changes, via the rods 382, 384, the distance between the first frame 100 and the second frame 200. As a result, a translational adjusting movement of the interface 230 and, therefore of the treatment block or tool, can be achieved using the third setting wheel 320.

Figure 10:
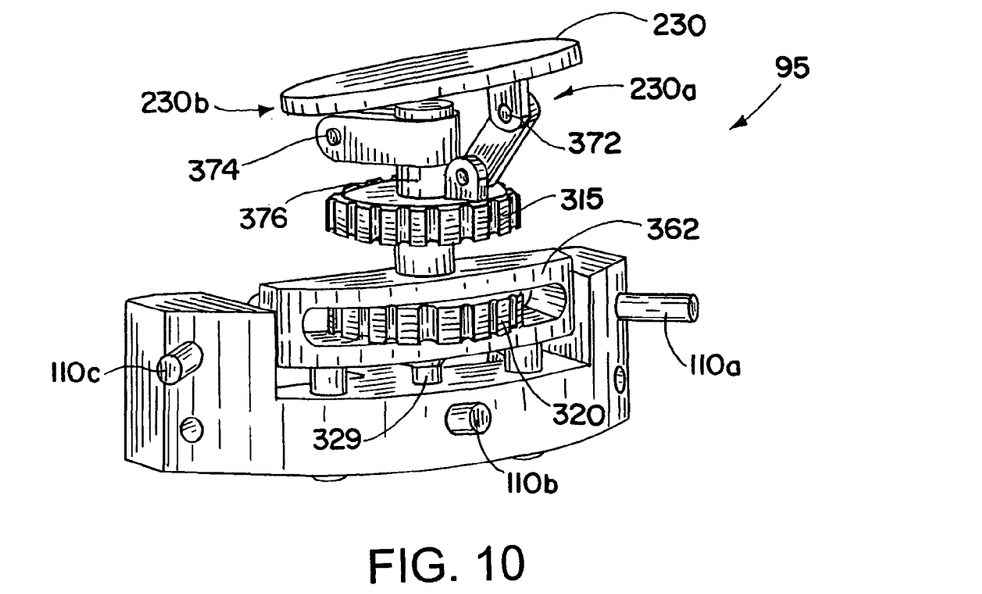
FIG. 10 is an isometric view of the treatment aid in accordance with another embodiment of the invention, wherein the interface is in an inclined orientation.
Figure 11:
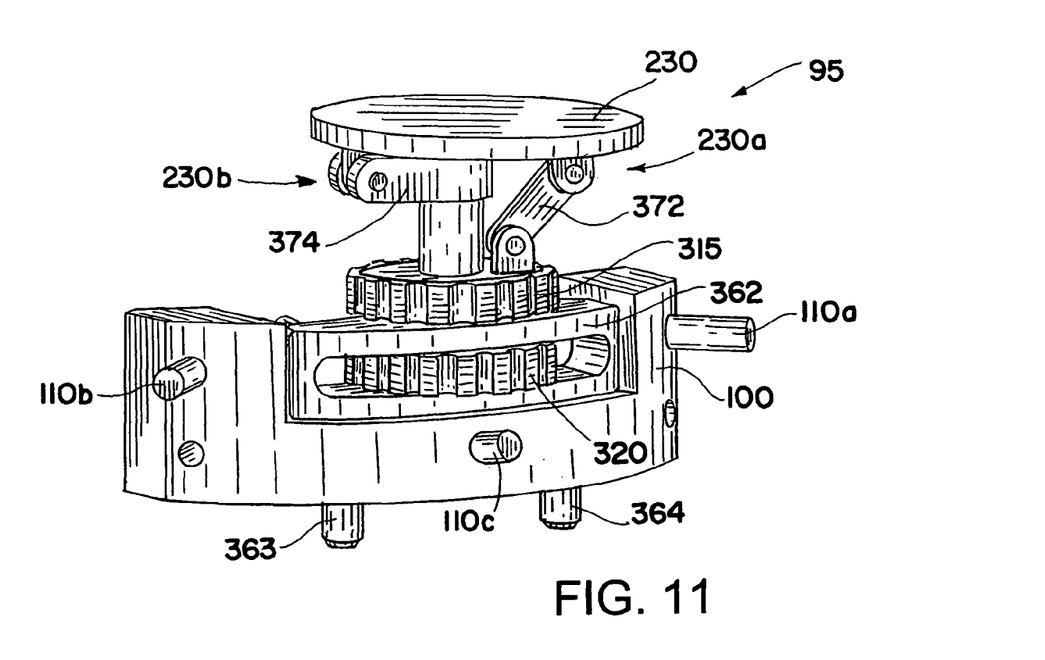
FIG. 11 is an isometric view of the embodiment of FIG. 10, wherein the interface is in a horizontal orientation.

FIGS. 10 and 11 show a fourth embodiment of the treatment aid 95. In this embodiment, one setting wheel 315 is utilized to rotate the interface 230 and, therefore, the treatment block or tool about two rotational axes.

The interface 230 can be formed as a plate-like structure, e.g. a round plate having a flat surface, and the first setting wheel 315 can be connected to a first side 230a of the interface 230 via a joint connection 372. A second side 230b of the interface 230, preferably a side opposite the first side 230a, can be connected to a threaded rod 376 via a joint connection 374. The first setting wheel 315 can have an inner thread which meshes or otherwise interfaces with an outer thread of the threaded rod 376. As the first setting wheel 315 is rotated, it travels along the rod 376. As the first setting wheel 315 moves toward the interface 230, the interface 230 is increasingly inclined via the joint connection 372. Simultaneously, the interface 230, by virtue of the joint connection 372, is rotated along with the first setting wheel 315. As the first setting wheel 315 is rotated, the interface 230 rotates about a rotational axis corresponding to the axis of the threaded rod 376. Thus, many different inclinations of the interface 230 about two rotational axes perpendicular to each other can be set.

While FIG. 10 shows the interface 230 in an inclined orientation, FIG. 11 shows the interface in a level orientation. The translational movement can again be achieved via a second setting wheel 320. The first frame 100 includes positioning pins 110a, 110b and 110c which can be driven into a bone. The adjusting device of the present embodiment includes an intermediary frame structure 362, which serves the translational movement. The intermediary frame structure 362 also is guided in the frame 100 by pins 363 and 364 in complementary cylindrical bores. The distance between the intermediary frame 362 and the first frame 100 can be set by rotating the second setting wheel 320. The second setting wheel 320 is connected, secured against rotation, to a threaded rod 329, which meshes with a complementary thread in the first frame 100. The second setting wheel 320 slaves the intermediary frame structure 362, which in turn is mounted in the first frame 100 via pins 362, 364, secured against rotation but such that it can move translationally. The threaded rod 376 is fixedly connected to the intermediary frame 362, such that the translational movement of the intermediary frame 362 is transferred onto the interface 230. The distance between the second setting wheel 320 and the first frame 100 can be changed by rotating the second setting wheel 320.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An adjustable treatment aid for guiding, holding, attaching and/or positioning a tool for treating a bone, comprising:
    a first frame that is attachable to the bone;
    a second frame for guiding, holding, attaching and/or positioning the tool; and
    at least one adjusting device that allows the first frame to be spatially adjusted relative to the second frame along at least one degree of freedom, wherein the adjusting device includes
        a support member connecting the first frame to the second frame, said support member configured to enable movement of the first frame relative to the second frame about at least two non-parallel axes,
        at least one resiliently deformable element connecting the second frame to the first frame, such that deflection of the deformable element corresponds to the at least one degree of freedom, and
        at least one setting member operative to cause resilient deflection of the deformable element to effect a corresponding positional adjustment of the second frame relative to the first frame along the at least one degree of freedom.

2. The treatment aid of claim 1, wherein the adjusting device exhibits three adjustment degrees of freedom.

3. The treatment aid of claim 1, further comprising a second adjusting device configured for translational movement of the first frame relative to the second frame.

4. The treatment aid of claim 1, wherein the at least one adjusting device includes a locking mechanism that inhibits relative movement between the first and second frames.

5. The treatment aid of claim 1, wherein the support member comprises at least one rotary joint between the first and second frame that enables movement about the at least two non-parallel axes.

6. The treatment aid of claim 1, further comprising the tool, said tool being fixed, releaseably coupled or integrally formed with the second frame.

7. The treatment aid of claim 1, further comprising a trackable device for determining a position of the tool.

8. The treatment aid of claim 7, wherein the trackable device is a reference star, the reference star comprising a plurality of markers.

9. The treatment aid of claim 8, wherein the reference star further comprises a contact interface for contacting the treated bone, so as to verify a position of a treatment geometry.

10. The treatment aid of claim 1, wherein the tool is at least one of an incision block, a drilling template, a drill, and an incision tool.

11. The treatment aid of claim 1, wherein the at least one setting member comprises at least one setting wheel operative to control a force applied to the at least one deformable element, and as the at least one setting wheel is rotated, the force is increased or decreased.

12. The treatment aid of claim 11, wherein the at least one setting wheel controls a rotational movement.

13. An adjustable treatment aid for guiding, holding, attaching and/or positioning a tool for treating a bone, comprising:
    a first frame that includes a fixing device for attaching the first frame to the bone;
    a second frame for guiding, holding, attaching and/or positioning the tool; and
    at least one adjusting device that allows the first frame to be spatially adjusted relative to the second frame along at least one degree of freedom,
    wherein the adjusting device comprises
    a first casing having a first surface;
        a first sealing element, wherein the first sealing element can slide air tight along an inner wall of the first casing;
    a deformable element; and
    a first elastic element, wherein the first elastic element provides a first force that tends to urge the deformable element onto the first surface, thereby deforming the deformable element and inhibiting spatial adjustment along at least a first degree of freedom.

14. The treatment aid of claim 13, wherein when air pressure or hydraulic pressure is introduced into the first casing, the pressure tends to push the first sealing element in a direction that counteracts the first force of the first elastic element, thereby removing the deformation of the deformable element and allowing spatial adjustment along the at least first degree of freedom.

15. An adjustable treatment aid for guiding, holding, attaching and/or positioning a tool for treating a bone, comprising:
    a first frame that includes a fixing device for attaching the first frame to the bone;
    a second frame for guiding, holding, attaching and/or positioning the tool; and
    at least one adjusting device that allows the first frame to be spatially adjusted relative to the second frame along at least one degree of freedom, wherein the adjusting device further comprises
    a spherical element having a first diameter, the spherical element being fixedly connected to at least one axis of the adjusting device;
    a second casing, wherein the second casing includes a spherical opening having a second diameter, and the spherical element interfaces with the spherical opening;
    a sliding element having a meshing tip, wherein the sliding element slides air tight along an inner wall of the second casing;
    an elastic element, wherein the elastic element provides a force that tends to urge the meshing tip onto the spherical element, thereby inhibiting spatial adjustment along at least a second degree of freedom.

* * * * *